United States Patent [19]
Masaki et al.

[11] Patent Number: 6,030,766
[45] Date of Patent: Feb. 29, 2000

[54] ORGAN PRESERVATION COMPOSITION COMPRISING NICARAVEN AND METHODS OF USE

[75] Inventors: Yoshihiko Masaki, Tokyo; Kazuo Kumano, Kanagawa-ken, both of Japan

[73] Assignee: Chugai Seiyaku Kabushiki Kaisha, Tokyo, Japan

[21] Appl. No.: 08/976,580

[22] Filed: Nov. 24, 1997

Related U.S. Application Data

[62] Division of application No. 08/537,785, filed as application No. PCT/JP94/00681, Apr. 25, 1994, abandoned.

[30] Foreign Application Priority Data

May 7, 1993 [JP] Japan ..................... 5-141110

[51] Int. Cl.[7] .............................. A01N 1/02; A01N 43/40
[52] U.S. Cl. .............................. 435/1.1; 435/1.2; 514/340
[58] Field of Search ....................... 435/1.1, 1.2; 514/340

[56] References Cited

U.S. PATENT DOCUMENTS 4,366,161  12/1982  Mori et al. .............................. 424/266

FOREIGN PATENT DOCUMENTS 3-101621  4/1991  Japan .
2 249 937  5/1992  United Kingdom .

OTHER PUBLICATIONS

Koide T., "Role of Peroxides in the Cerebral Transmembrane Ion Fluxes and Their Relevance to Ischemic Brain Edema", Bioelectrochemistry and Bioenergetics 18 : 307–324 (1987).

T. Kamezawa, Experimental Studies on the Pathophysiology and Effects of Drugs on Vasogenic Brain Edema with Specific Gravimetric Technique and Phosphorous–31 Magnetic Resonance Spectroscopy, Chemical Abstracts, vol. 45 No. 2, pp. 161–178, 1993.

Y. Mori et al, Experimental Studies on Nicaraven as radioprotector. Free radical Scavenging Effect and the Inhibition of Cellular Injury, Chemical Abstracts, vol. 53 No. 6, pp. 704–712, 1993.

Derwent Publications Ltd., Drug for Treating Ischaemic Heart Disease Contains Propylene DI Nicotinamide which Increases Rate of Myocardium Contraction and Lactic Acid Ingestion, Dec. 10, 1991. *Abstract*—JP 3–279328.

T. Koide, Role of Peroxides in the Cerebral Transombrane Ion Fluxes and their Relevance to Ischemic Brain Edema, Chemical Abstracts, vol. 18 No. 1–3, pp. 307–324, 1987.

Derwent Publications, Hydroxy Radical Scavenger Nicotinamide Nitrate for Treatment of Tumor Inflammation, Peptic Ulcer, Senility, Liver Dysfunction, Apr. 26, 1991. *Abstract* JP 3–101621.

T. Asano et al, Amelioration of Ischemic Cerebral Edema by a Free Radical Scavenger, Chemical Abstract, vol. 6 No. 4, pp. 163–168, 1984.

Asano T et al., Neurological Research 6:163–168 (1984).

*Primary Examiner*—Sandra E. Saucier
*Attorney, Agent, or Firm*—Browdy and Neimark

[57] ABSTRACT

An organ preservative or protective that are characterized by containing (±)-N,N'-propylenedinicotinamide as an active ingredient. The compound not only exhibits outstanding organ preserving and protecting effects: it is also free from any significant problems with side effects and safety aspects. Hence, it is very useful as an organ preservative and protective.

7 Claims, No Drawings

ORGAN PRESERVATION COMPOSITION COMPRISING NICARAVEN AND METHODS OF USE

This is a division of parent, application Ser. No. 08/537,785, nationalized Oct. 23, 1995, from PCT/JP/94/00681 filed Apr. 25, 1994, abandoned without prejudice upon the filing of the present divisional application.

TECHNICAL FIELD

This invention relates to organ preservatives and protectives that contain (±)-N,N'-propylenedinicotinamide (generic name; nicaraven) as an active ingredient.

BACKGROUND ART

Various drugs have heretofore been known to exhibit organ preserving or protecting actions [see, for example, Japanese Patent Domestic Announcement (kohyo) No. 502819/1986, Japanese Patent Public Disclosure (kokai) Nos. 267233/1987, 20/1989, 72432/1991, 101621/1991 and 43463/1993.

In particular, Japanese Patent Public Disclosure (kokai) No. 101621/1991 teaches that N-(2-hydroxyethyl) nicotinamide nitrate ester (generic name: nicorandil) having a hydroxy radical scavenging action is applicable as an organic preservative and protective.

Nicaraven has been known to be useful as a thrombolytic agent, anti-arteriosclerotic agent and as an anti-cerebral vasospasm agent [see Japanese Patent Publication (kokoku) No. 55911/1986] but there have been no reports that this compound exhibits an organ preserving or protecting action.

The various drugs heretofore known to have organ preserving or protecting actions are not completely satisfactory in their operational activity. Even with drugs that are by and large potent in their operational activity, problems are often encountered in such aspects as the side-effect and safety features of the drugs per se. Hence, very few have been commercialized as practical medicines.

DISCLOSURE OF INVENTION

The present inventors conducted intensive studies with a view to solving these problems of the prior art and found unexpectedly that nicaraven could be a solution that exhibited outstanding organ preserving and protecting effects. The present invention has been accomplished on the basis of this finding.

Nicaraven which is the active ingredient of the organ preservative and protective of the invention is a known compound and can be synthesized by the method described in Japanese Patent Publication (kokoku) No. 55911/1986.

The preservative and protective of the invention are applicable to all kinds of organs obtained from humans and other animals, which may be exemplified by the heart, kidneys, spleens, lungs and liver. The drugs of the invention can be used as additives to preserving solutions or perfusates in order to minimize the damage that can occur to organs during storage after they have been extracted from donors for surgical operations for organ transplantation. The drugs may also be administered to patients under transplantation as organ protectives which are intended to suppress or prevent the occurrence of rejections after organ transplantation. The use of the preservative of the invention has the added advantage that the extracted organ can be stored without deterioration so that its function is maintained until after the transplantation is complete. It should be mentioned that if the nicaraven preparation of the invention is to be used for preserving an extracted organ that is to be eventually transplanted in another person's body, it is effective to administer said preparation to the donor before surgical operation so that a specified amount of nicaraven is preliminarily incorporated into the cells of the organ to be transplanted.

BEST MODE FOR CARRYING OUT THE INVENTION

When the drug of the invention is to be used as an organ preservative or protective, nicaraven may be added either as such to a preserving solution or a perfusate or as a solution or suspension in various solvents that permit the nicaraven to be uniformly dissolved or dispersed.

Preferred examples of the solvents that may be used to this end include alcohols such as ethanol, propylene glycol, glycerin and polyethylene glycol, as well as water, physiological saline, triacetin and mixtures thereof in desired proportions. The solutions and suspensions of nicaraven in these solvents can be rendered aseptic by any suitable methods of sterilization such as filtration through bacteria-retaining filters, exposure to heat, addition of bactericides, and application of radiations. Alternatively, aseptic nicaraven may first be formulated either as such or as a solid preparation and then admixed with the above-mentioned solvents in an aseptic form just prior to use.

When nicaraven is to be used as an organ protective for suppression or preventing the occurrence of rejections after organ transplantation, it is administered either orally or parenterally such as by intrarectal, subcutaneous, intramuscular, intravenous, intra-arterial and transcutaneous routes; preferably, nicaraven is administered orally or intravenously.

For oral administration, nicaraven may be formulated as a solid or liquid preparation. Exemplary solid preparations include tablets, pills, powders and granules. Such solid preparations can be produced by mixing the active ingredient nicaraven with at lest one pharmaceutically acceptable carrier such as sodium hydrogencarbonate, calcium carbonate, starch, sucrose, mannitol and carboxymethyl cellulose. While common pharmaceutical formulation procedures may be employed, the preparations may contain other additives for formulation, such as lubricants exemplified by calcium stearate, magnesium stearate and glycerin.

Liquid preparations for oral administration include emulsions, solutions, suspensions, syrups and elixirs. These preparations may employ customarily used, pharmaceutically acceptable carriers such as water, and oleaginous bases such as liquid paraffin, coconut oil, fractionated coconut oil, soybean oil and corn oil.

For oral administration, the above-mentioned solid preparations may be formulated as enteric preparations by application of enteric coats which are formed by spraying solutions of enteric substances in either organic solvents or water; exemplary enteric substances include cellulose acetate phthalate, hydroxypropyl methyl cellulose phthalate, polyvinyl alcohol phthalate, styrene-maleic anhydride copolymer, and methacrylic acid-methyl methacrylate copolymer. Enteric solid preparations such as powders and granules may be encapsulated.

Other pharmaceutically acceptable carriers include optionally used adjuvants, fragrances, stabilizers and antiseptics.

Liquid preparations of powders may be administered in capsules that are made from gelatin and other absorbable substances.

Solid preparations for intrarectal administration include suppositories that contain nicaraven and which are produced by methods known per se.

The preparations for parenteral administration can be aseptic aqueous or non-aqueous solutions, suspensions or emulsions. The non-aqueous solutions or suspensions employ pharmaceutically acceptable carriers which are typically selected from among propylene glycol, polyethylene glycol, vegetable oils such as olive oil, and injectable organic esters such as ethyl oleate. These preparations may also contain adjuvants such as antiseptics, wetting agents, emulsifiers, dispersants and stabilizers. These solutions, suspensions and emulsions can be rendered aseptic by any suitable methods of sterilization such as filtration through bacteria-retaining filters, exposure to heat, addition of bactericides and application of radiations. Alternatively, aseptic solid preparations may first be produced and dissolved in sterile water or solutions for injection just prior to use.

Dosage forms for percutaneous administration include ointments and may be shaped by customary methods.

The dose of application of the drugs of the invention to be used as organ preservatives depends on various factors such as the type of the organ, whether it is subjected to simple preservation or perfusion, or the condition of the organ to be transplanted and its weight. Normally, the drugs are used such that their concentration in a preserving solution or a perfusate ranges from $10^{-12}$ to $10^{-2}$ mg/ml, preferably from $10^{-5}$ to $10^{-3}$ mg/ml. If the drugs of the invention are to be used as organ protectives for suppressing or preventing the occurrence of rejections after organ transplantation, the dose of their application also depends on various factors such as the subject to be treated by their administration, his or her age, sex, body weight and the route of administration. Normally, such drugs can be administered in daily doses of about 0.01 µg to 100 mg per kilogram of body weight.

The following examples are provided for the purpose of further illustrating the present invention but are in no way to be taken as limiting.

EXAMPLE

SD male rats (weighing about 350 g) were anesthetized intraperitoneally with pentobarbital (50 mg/kg), and medisected in the abdomen, followed by insertion of a catheter (0.26 ml or 0.61 ml) through the right ureter of each animal. Subsequently, heparinized physiological saline was injected into the vein of each animal through a catheter (22 G) inserted into the right renal artery, followed by initial perfusion with heparinized physiological saline (10 ml). Immediately thereafter, UW (University of Wisconsin) solution (20 ml) was infused and the kidneys were extracted. The extracted kidneys were immersed in a preserving solution containing UW solution and kept at 4° C. for 48 h. The kidneys were then subjected to isolated perfusion for 90 min. with an IPK (isolated perfused kidney) apparatus (Model KN-87N of NATSUME SEISAKUSHO CO., LTD.). The volume of perfusate and urine were measured at 30-min intervals. Portion of the perfusate and urine collected were used for biochemical analysis. The animals under experiment were divided into two groups. After medisection in the abdomen, the rats of group I were injected intravenously with nicaraven (3 mg). Ten minutes later, the kidneys were perfused with UW solution containing nicaraven (28 mg/100 ml) and preserved under cold conditions. After medisection in the abdomen, the rats of group II were injected intravenously with physiological saline. Ten minutes later, the kidneys were perfused with UW solution and preserved under cold conditions. The results are shown in Tables 1–5 below.

TABLE 1

Urine Volumes in IPK Preparation during Preservation Period

| | Control (group II) | | | Nicaraven treated (group I) | | |
|---|---|---|---|---|---|---|
| | 30 min | 60 min | 90 min | 30 min | 60 min | 90 min |
| 1 | 0.02 | 0.05 | 0.14 | 0.94 | 1.16 | 0.70 |
| 2 | 0.06 | 0.06 | 0.06 | 1.91 | 2.89 | 4.40 |
| 3 | 0.28 | 0.14 | 0.18 | 0.50 | 0.51 | 0.53 |
| 4 | 0.20 | 0.14 | 0.14 | 1.20 | 1.33 | 2.02 |
| 5 | 0.06 | 0.07 | 0.07 | 0.45 | 0.73 | 1.64 |
| 6 | 0.07 | 0.03 | 0.04 | 0.89 | 1.11 | 0.86 |
| | 0.16 ± 0.10 | 0.08 ± 0.05 | 0.11 ± 0.06 | 0.98 ± 0.54 | 1.29 ± 0.84 | 1.69 ± 1.45 |
| | | | | $p < 0.005$ | $p < 0.005$ | $p < 0.005$ |

TABLE 2

Perfusate Volumes in IPK Preparation during Preservation Period

| | Control (group II) | | | Nicaraven treated (group I) | | |
|---|---|---|---|---|---|---|
| | 30 min | 60 min | 90 min | 30 min | 60 min | 90 min |
| 1 | 0.02 | 0.05 | 0.14 | 0.94 | 1.16 | 0.70 |
| 2 | 0.06 | 0.06 | 0.06 | 1.91 | 2.89 | 4.40 |
| 3 | 0.28 | 0.14 | 0.18 | 0.50 | 0.51 | 0.53 |
| 4 | 0.20 | 0.14 | 0.14 | 1.20 | 1.33 | 2.02 |
| 5 | 0.06 | 0.07 | 0.07 | 0.45 | 0.73 | 1.64 |

TABLE 2-continued

Perfusate Volumes in IPK Preparation during Preservation Period

| | Control (group II) | | | Nicaraven treated (group I) | | |
|---|---|---|---|---|---|---|
| | 30 min | 60 min | 90 min | 30 min | 60 min | 90 min |
| 6 | 0.07 | 0.03 | 0.04 | 0.89 | 1.11 | 0.86 |
| | 0.16 ± 0.10 | 0.08 ± 0.05 | 0.11 ± 0.06 | 0.98 ± 0.54 | 1.29 ± 0.84 | 1.69 ± 1.45 |
| | | | | $p < 0.005$ | $p < 0.005$ | $p < 0.005$ |

TABLE 3

Urinary Sodium Contents in IPK Preparation during Preservation Period

| | Control (group II) | | | Nicaraven treated (group I) | | |
|---|---|---|---|---|---|---|
| | 30 min | 60 min | 90 min | 30 min | 60 min | 90 min |
| 1 | 3.3 | 3.5 | 3.8 | 3.1 | 3.2 | 3.4 |
| 2 | 3.3 | 3.6 | 3.8 | 3.4 | 3.3 | 3.4 |
| 3 | 3.5 | 3.7 | 3.8 | 3.1 | 3.5 | 3.4 |
| 4 | 3.2 | 3.6 | 3.6 | 3.3 | 3.2 | 3.2 |
| 5 | 3.2 | 3.8 | 3.8 | 3.3 | 3.1 | 2.6 |
| 6 | 3.3 | 3.5 | 3.8 | 3.2 | 3.3 | 3.4 |
| | 3.3 ± 0.11 | 3.6 ± 0.12 | 3.7 ± 0.10 | 3.2 ± 0.12 | 3.3 ± 0.14 | 3.2 ± 0.32 |
| | | | | | $p < 0.01$ | $p < 0.005$ |

TABLE 4

Urinary Potassium Contents in IPK Preparation during Preservation Period

| | Control (group II) | | | Nicaraven treated (group I) | | |
|---|---|---|---|---|---|---|
| | 30 min | 60 min | 90 min | 30 min | 60 min | 90 min |
| 1 | 1.01 | 0.33 | 0.33 | 0.35 | 0.24 | 0.26 |
| 2 | 0.82 | 0.33 | 0.31 | 0.27 | 0.27 | 0.27 |
| 3 | 0.92 | 0.35 | 0.33 | 0.41 | 0.27 | 0.27 |
| 4 | 0.55 | 0.29 | 0.27 | 0.45 | 0.27 | 0.26 |
| 5 | 0.99 | 0.33 | 0.31 | 0.29 | 0.27 | 0.21 |
| 6 | 1.15 | 0.29 | 0.33 | 0.30 | 0.27 | 0.27 |
| | 0.91 ± 0.21 | 0.32 ± 0.02 | 0.31 ± 0.02 | 0.35 ± 0.07 | 0.27 ± 0.01 | 0.25 ± 0.02 |
| | | | | $p < 0.005$ | $p < 0.005$ | $p < 0.01$ |

TABLE 5

Urinary Creatinine Contents in IPK Preparation during Preservation Period

| | Control (group II) | | | Nicaraven treated (group I) | | |
|---|---|---|---|---|---|---|
| | 30 min | 60 min | 90 min | 30 min | 60 min | 90 min |
| 1 | 2.0 | 2.0 | 2.0 | 2.0 | 2.0 | 2.0 |
| 2 | 2.0 | 2.0 | 2.0 | 2.0 | 2.0 | 2.0 |
| 3 | 3.0 | 3.0 | 3.0 | 2.0 | 2.0 | 2.0 |
| 4 | 3.0 | 3.0 | 3.0 | 2.0 | 2.0 | 2.0 |
| 5 | 3.0 | 3.0 | 3.0 | 2.0 | 2.0 | 2.0 |
| 6 | 3.0 | 3.0 | 3.0 | 2.0 | 2.0 | 2.0 |
| | 2.7 ± 0.5 | 2.7 ± 0.5 | 2.7 ± 0.5 | 2.0 ± 0 | 2.0 ± 0 | 2.0 ± 0 |
| | | | | $p < 0.05$ | $p < 0.05$ | $p < 0.05$ |

INDUSTRIAL APPLICABILITY OF THE INVENTION

Nicaraven not only exhibits outstanding organ preserving and protecting effects: it is also free from any significant problems with side-effect and safety aspects. Therefore, nicaraven is very useful as an organ preservative and protective.

We claim:

1. In a combination of a liquid carrier composition for preserving an extracted organ and said extracted organ immersed therein, said composition comprising
a mixture of an active agent and a liquid carrier in an amount sufficient to immerse said extracted organ therein, the improvement wherein
said active agent is (±)-N,N'-propylene-dinicotinamide.

2. A combination according to claim 1 wherein said carrier comprises a solvent selected from the group consisting of ethanol, propylene glycol, glycerin, polyethylene glycol, triacetin and, mixtures thereof together with water or physiological saline.

3. An organ protective liquid composition adapted to be administered to a human patient under transplantation conditions, comprising a pharmaceutical carrier and (±)-N, N'-propylenedinicotinamide as an active ingredient in an amount of 28 mg/100 ml, in a unit dosage form of size adequate for administration to a human to provide a transplantation protective effect.

4. A method comprising administering a composition to a patient during transplantation or immediately prior to transplantation of a human organ, by oral, intrarectal, subcutaneous, intramuscular, intravenous, intra-arterial or transcutaneous route, said composition comprising a carrier and an amount effective for protecting said human organ of (±)-N,N'-propylenedinicotinamide as an active ingredient.

5. A method according to claim 4 wherein said administration is at a daily dosage of about 0.01 µg to 100 mg per kg of body weight.

6. A method of protecting an organ during removal or transplantation of the organ, comprising:

administering to the organ donor during the removal of the organ, or to the organ recipient during or immediately prior to the transplantation of the organ, (±)-N,N'-propylenedinicotinamide in an amount of 0.01 µg to 100 mg/kg of body weight of the donor or recipient, wherein the administration to the donor or recipient is by oral, rectal, subcutaneous, intramuscular, intravenous, intra-arterial or transcutaneous route.

7. A method of preserving a human organ after removal thereof and prior to transplantation of the organ, comprising placing said organ within a composition of an active agent and a liquid carrier, said composition being present in a quantity sufficient for said extracted organ to be immersed within said composition, and wherein said active agent is (±)-N,N'-propylenedinicotinamide.

* * * * *